(12) United States Patent
Nolte et al.

(10) Patent No.: US 12,117,411 B2
(45) Date of Patent: Oct. 15, 2024

(54) METHODS FOR ANALYZING A GAS MIXTURE AND GAS SENSOR

(71) Applicant: Robert Bosch GmbH, Stuttgart (DE)

(72) Inventors: Philipp Nolte, Gerlingen (DE); Katrin Luckert, Leonberg (DE); Maria Martinez Prada, Aidlingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 478 days.

(21) Appl. No.: 17/312,270

(22) PCT Filed: Dec. 6, 2019

(86) PCT No.: PCT/EP2019/083929
§ 371 (c)(1),
(2) Date: Jun. 9, 2021

(87) PCT Pub. No.: WO2020/120299
PCT Pub. Date: Jun. 18, 2020

(65) Prior Publication Data
US 2022/0034835 A1  Feb. 3, 2022

(30) Foreign Application Priority Data

Dec. 14, 2018  (DE) .......................... 102018221760.2

(51) Int. Cl.
*G01N 27/12* (2006.01)
*G01N 33/00* (2006.01)

(52) U.S. Cl.
CPC ....... *G01N 27/124* (2013.01); *G01N 33/0044* (2013.01)

(58) Field of Classification Search
CPC ............. G01N 27/124; G01N 33/0044; G01N 27/128; G01N 27/123; G01N 33/0016; G08B 17/117
See application file for complete search history.

(56) References Cited

U.S. PATENT DOCUMENTS

| 4,567,475 A | * | 1/1986 | Bukowiecki | ......... G01N 27/124 |
| | | | | 73/31.06 |
| 2016/0216227 A1 | | 7/2016 | Boni | |
| 2016/0349201 A1 | * | 12/2016 | Graunke | ............ G01N 33/0016 |

FOREIGN PATENT DOCUMENTS

| CN | 1478201 A | 2/2004 |
| CN | 103718031 A | 4/2014 |

(Continued)

OTHER PUBLICATIONS

International Search Report for PCT/EP2019/083929, Issued Feb. 27, 2020.

*Primary Examiner* — Stephen Hobson
(74) *Attorney, Agent, or Firm* — NORTON ROSE FULBRIGHT US LLP; Gerard A. Messina

(57) ABSTRACT

A method for analyzing a gas mixture, in which a layer which is configured for the adsorption and/or absorption of components of the gas mixture is exposed to the gas mixture. The method includes cooling the layer from a first to a second temperature and heating the layer from the second to a third temperature. While the layer has the first, second, and third temperature, at least one electrical resistance value of the layer is measured. A method is described in which a first and second layer are exposed to the gas mixture. The first layer is cooled from a first to a second temperature and the second layer is cooled from a third to a fourth temperature. While the first layer has the first and second temperature and the second layer has the third and fourth temperature, at least one electrical resistance value of the respective layer is measured.

16 Claims, 4 Drawing Sheets

(56) References Cited

FOREIGN PATENT DOCUMENTS

| | | |
|---|---|---|
| DE | 19543296 A1 | 5/1997 |
| DE | 102017206202 A1 | 10/2018 |
| EP | 2995938 A1 | 3/2016 |
| JP | 2007024508 A | 2/2007 |

* cited by examiner

METHODS FOR ANALYZING A GAS MIXTURE AND GAS SENSOR

FIELD

The present invention relates to methods for analyzing a gas mixture. Furthermore, the present invention relates to a computer program which is configured to carry out each step of such a method, and a machine-readable memory medium, on which the computer program is stored. The present invention also relates to gas sensors which are configured to analyze a gas mixture.

BACKGROUND INFORMATION

Metal oxide sensors may be used to detect sulfurous substances in a gas mixture. The fact is utilized that the adsorption of these gas components on or the absorption of these gas components in a metal oxide layer changes its electrical resistance. If the metal oxide layer is exposed to the gas mixture, the components of the gas mixture may thus be inferred from the measured electrical resistance of the layer. Since the effect of different gas components on the electrical conductivity is temperature dependent, such measurements are carried out by heating the metal oxide layer at a defined temperature.

European Patent Application No. EP 2 995 938 A1 describes such a metal oxide sensor and a method for analyzing the components of a gas mixture. The sensor and the method are used in particular for analyzing a breath sample. In this way, the detection of, among other things, hydrogen sulfide in the breath is carried out. Tin oxide is used as the metal oxide layer.

Such a method is not always capable, however, of recognizing a mixture of different sulfurous compounds. Thus, for example, hydrogen sulfide may result in a reduction of the electrical resistance of tin oxide, while dimethyl disulfide increases the electrical resistance of tin oxide. If both compounds are contained in the gas mixture, their effects on the electrical resistance of the tin oxide may thus compensate one another, so that the metal oxide sensor recognizes a gas mixture which is apparently free of sulfurous compounds.

SUMMARY

In accordance with an example embodiment of the present invention, in a method for analyzing a gas mixture, a layer which is configured for the adsorption and/or absorption of components of the gas mixture is exposed to the gas mixture. The layer is preferably a metal oxide layer, since the sensitivity of metal oxide layers, in particular with respect to sulfurous compounds, is known. It preferably includes at least one metal oxide, which is selected from the group made up of tin oxide, zinc oxide, tungsten (VI) oxide, and mixtures thereof. It particularly preferably contains at least 10 wt. % tin oxide, very particularly preferably at least 50 wt. % tin oxide. To still further improve the sensitivity of the layer, in particular with respect to sulfurous compounds, it is additionally preferred that it contains palladium and/or platinum, for example, 0.05 wt. % to 5 wt. %. These metals may be present in particular in the form of a doping or as nanoparticles in metallic or in oxidic form in the layer.

While the layer has a first temperature, at least one electrical resistance value of the layer is measured. Subsequently, its temperature is reduced from the first temperature to a second temperature. While the layer has the second temperature, at least one electrical resistance of the layer is measured again. The temperature of the layer is thereafter increased from the second temperature to a third temperature. At least one electrical resistance value of the layer is also measured at the third temperature. The components of the gas mixture are analyzed on the basis of the measured electrical resistance values.

This example method is based on the finding that a differentiation of different components of the gas mixture is facilitated if resistance values are measured at at least three different temperatures, these temperatures including at least one temperature pulse with reduction of the temperature of the layer.

In accordance with an example embodiment of the present invention, this may be implemented particularly advantageously in that the temperature of the layer is furthermore reduced from the third temperature to a fourth temperature and at least one electrical resistance value of the layer is also measured at the fourth temperature. The analysis is also based on this resistance value. The first temperature differs from the third temperature and/or the second temperature differs from the fourth temperature. A binary temperature pulse is thus generated, which is made up of a first temperature pulse and a second temperature pulse. The second temperature pulse differs at least with respect to its starting temperature or with respect to its end temperature from the first temperature pulse. Components of a gas mixture which, in a defined temperature pulse, display effects on the electrical resistance of the layer, which could compensate one another, display a deviating behavior in the second temperature pulse, however, which enables the identification of the components. By using a characteristic map in which the behavior of the substances is stored, they may even be quantified.

It is preferred for the temperature of the layer to be increased from the fourth temperature to the first temperature after the measurement of the electrical resistance value at the fourth temperature. This enables the method to be carried out periodically. The period length is to be in particular in the range from 20 seconds to 120 seconds to obtain a reliable analysis result.

A further method for analyzing the gas mixture in accordance with an example embodiment of the present invention provides that a first layer and a second layer are exposed to the gas mixture. The same materials are preferred for both layers as in the above-described method. In this method, at least one electrical resistance of the first layer is measured while it has a first temperature. Subsequently, the temperature of the first layer is reduced from the first temperature to a second temperature and at least one electrical resistance value of the first layer is again measured at the second temperature. Moreover, at least one electrical resistance value of the second layer is measured while it has a third temperature. The temperature of the second layer is reduced from the third temperature to a fourth temperature and at least one electrical resistance value of the second layer is also measured at the fourth temperature. The first temperature differs from the third temperature and/or the second temperature differs from the fourth temperature. The components of the gas mixture are analyzed on the basis of the measured electrical resistance values. This method also provides the evaluation of two temperature pulses. However, these are not generated on the same layer, but on two different layers. The electrical resistance values of the first temperature pulse and the second temperature pulse may accordingly be measured at the same time, which enables the method to be carried out faster.

The at least one electrical resistance value of the layer, while it has the second temperature, is preferably measured after the layer has been held at the second temperature for a time period which is in the range from 5 seconds to 30 seconds. Thus, on the one hand, a sufficiently long exposure of the layer to the gas mixture takes place at this temperature, so that many gas components may be adsorbed on the surface or absorbed therein. On the other hand, this time period is also short enough to avoid saturation effects. If the method provides that a measurement is also to be carried out at a fourth temperature, this preferably also takes place after the layer has been held at this temperature for a time period in the range from 5 seconds to 30 seconds.

The at least one electrical resistance value of the layer, while it has the first temperature and the third temperature, is preferably measured after the layer has been held at the particular temperature for a time period of at least 100 ms, preferably at least 1000 ms. An at least partial desorption of gas components takes place in this time period, which have previously been adsorbed or absorbed at a lower temperature.

In accordance with an example embodiment of the present invention, it is furthermore preferred if the increase of the temperature of the layer from the second temperature to the third temperature takes place within at most one second, particularly preferably within less than 200 ms. The temperature increase is preferably to be at least 20 K. Both sulfurous compounds, for example hydrogen sulfide, which result in a reduction of the resistance value at a lower temperature, and sulfurous compounds, for example dimethyl sulfide, which result in an increase of the resistance of the layer at lower temperature, result in a resistance decrease shortly after such a sudden change to a higher temperature. The disadvantage of the ambiguity due to a mutual cancellation at a low second or fourth temperature may thus be avoided. After the temperature jump, the individual components contribute with a signal in the same resistance-decreasing direction. A sum signal is therefore achieved, the individual components certainly being able to have a separate weighting. The higher the concentration of each of the components, the stronger the signal change is. If the method also provides a measurement at the fourth temperature, alternatively or additionally to the temperature increase from the second temperature to the third temperature, this temperature jump may also take place in the case of the temperature increase from the fourth temperature to the first temperature.

The first temperature and the third temperature are each preferably in a range from 250° C. to 400° C. The first temperature and the third temperature may be equal or different. These high temperatures enable a "bake-out" of the layer, to thus desorb components of the gas mixture adsorbed or absorbed at a prior, lower temperature.

The second temperature is preferably in the range from 20° C. to 200° C. If a measurement is also provided at a fourth temperature, the fourth temperature is thus preferably also in the range from 20° C. to 200° C., it being able to be equal to the second temperature or different from the second temperature.

If the first temperature and the third temperature are equal, it is provided in one preferred specific embodiment of the present invention that these two temperatures are in the range from 300° C. to 400° C., the second temperature is in the range from 30° C. to 100° C., and the fourth temperature is in the range from 100° C. to 180° C. In this case, gas components which reduce the resistance value, such as hydrogen sulfide, predominantly contribute to the measured electrical resistance value at the second temperature, for example, while at the fourth temperature, all gas components contribute to the measured resistance value.

In accordance with an example embodiment of the present invention, it is preferred if the gas mixture contains at least two different sulfurous components, which are selected in particular from the group which is made up of hydrogen sulfide, methyl mercaptan, dimethyl sulfide, and dimethyl disulfide. The method enables the simultaneous determination of multiple such gas components in parallel. The proportion of these sulfurous components in the gas mixture is preferably 1-500 ppb, particularly preferably 5-200 ppb. Still other volatile organic substances, for example alcohols or ketones, may additionally be contained in the gas mixture. Their proportion in the gas mixture is preferably 10 ppb to 10 ppm, particularly preferably 10 ppb to 2 ppm. It may originate from completely different sources, for example, the breath of humans or animals, bodily excretions, foods, or food residues. However, protective gas atmospheres having a reduced oxygen component may also be provided.

In accordance with an example embodiment of the present invention, the computer program is configured to carry out each step of the method, in particular when it runs on an electronic computer. It enables the implementation of different specific embodiments of the method in a gas sensor, without having to carry out structural modifications thereon. For this purpose, it is stored on the machine-readable memory medium. By loading the computer program onto the computer of a conventional gas sensor including a layer which is configured for adsorbing and/or absorbing components of a gas mixture, for example a gas sensor as described in European Patent Application No. EP 2 995 938 A1, a gas sensor is obtained which is configured to analyze a gas mixture with the aid of one of the methods.

BRIEF DESCRIPTION OF THE DRAWINGS

Exemplary embodiments of the present invention are shown in the figures and are explained in greater detail in the following description.

DETAILED DESCRIPTION OF EXAMPLE EMBODIMENTS

Figure 1:
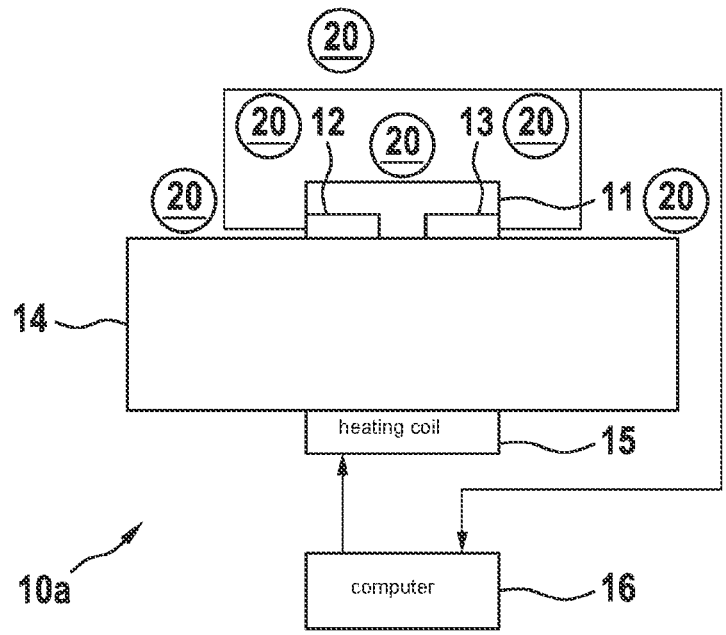
FIG. 1 schematically shows a gas sensor which may be used in the method according to one exemplary embodiment of the present invention.

Gas sensor 10a shown in FIG. 1 includes a sensitive layer 11, which is made up in the present case of tin oxide doped using palladium. A first electrode 12 and a second electrode 13 are situated in sensitive layer 11 in such a way that they may measure its electrical resistance. Sensitive layer 11 and electrodes 12, 13 are situated on one side of a substrate 14, on the opposite side of which a heating coil 15 is situated. This is controlled by a computer 16. Computer 16 additionally reads the voltage applied between electrodes 12, 13 and the current present in a circuit including electrodes 12, 13, so that the electrical resistance of layer 11 may be ascertained. Layer 11 is exposed to a gas mixture which contains components 20. In the exemplary embodiments of the method according to the present invention described hereinafter, these components include hydrogen sulfide and dimethyl disulfide, which are differentiated with the aid of the different specific embodiments of the method.

In a conventional method for analyzing components 20, as is described in European Patent Application No. EP 2 995 938 A1, layer 11 is initially heated for a predefined time period of, for example, 20 seconds to a first temperature $T_1$ of, for example, 300° C., in that heating coil 15 is activated.

Figure 2:
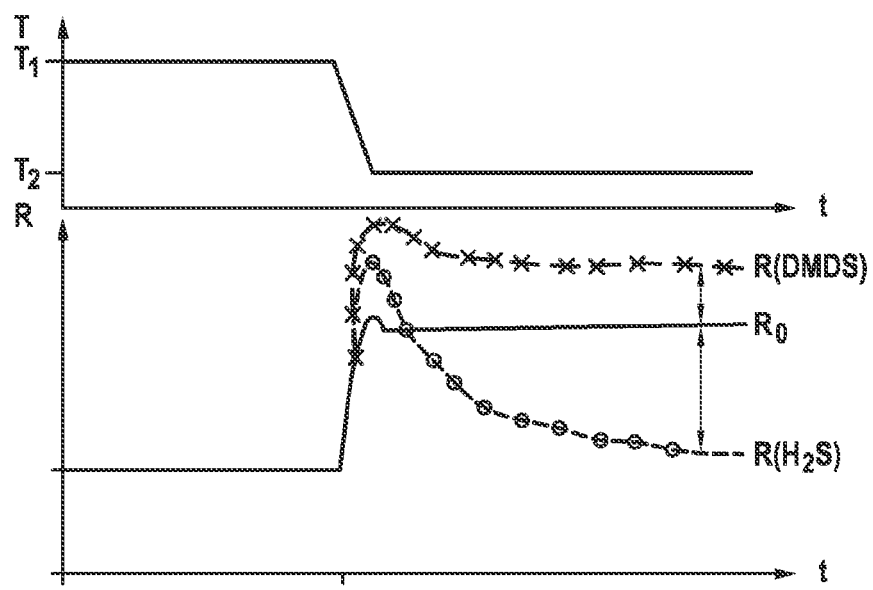
FIG. 2 shows in two diagrams the temporal curve of the temperature and the electrical resistance of a metal oxide layer in an exemplary embodiment of the method according to the present invention.

Subsequently, temperature T is reduced to a second temperature $T_2$ of, for example, 100° C. If the gas mixture did not contain sulfurous components, a curve of electrical resistance R with time t according to resistance profile $R_o$ shown in FIG. 2 would be expected. If the gas mixture contained hydrogen sulfide ($H_2S$) as the only sulfurous component, in contrast, a reduction of resistance R according to resistance profile $R(H_2S)$ would be expected. In contrast, if the gas mixture contained dimethyl disulfide (DMDS) as the only sulfurous component, an increase of resistance R according to resistance profile R(DMDS) would be expected. However, if the gas mixture contains both components, these effects may cancel each other out, so that resistance profile $R_0$ again results. Gas sensor 10a would thus incorrectly indicate a gas mixture which does not contain sulfurous components.

In one exemplary embodiment of the method according to the present invention, layer 11 is initially heated for two seconds to a temperature $T_1$ of 300° C. and then reduced to a temperature $T_2$ of 50° C. Resistance R of layer 11 is measured immediately before reducing temperature T and 20 seconds after its reduction.

Figure 3:
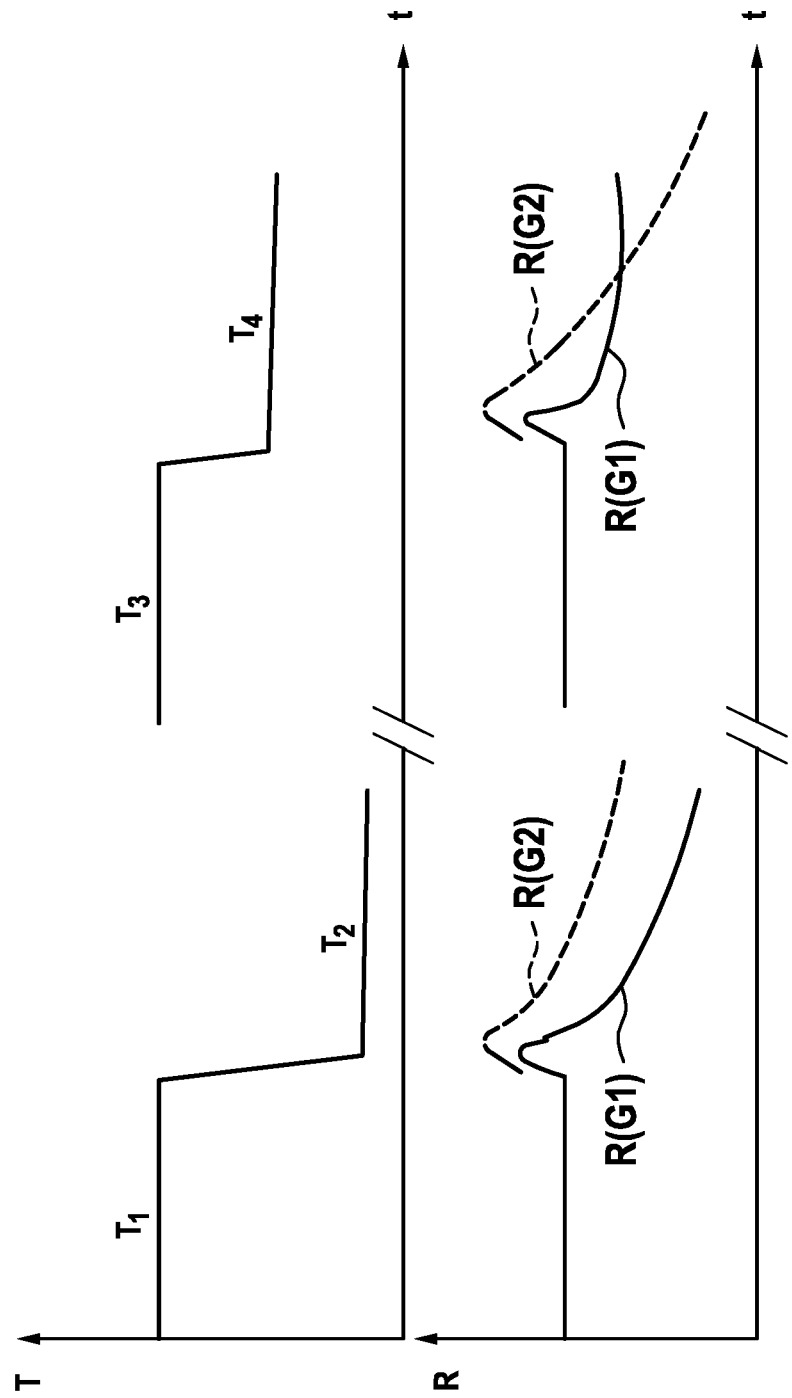
FIG. 3 shows in two diagrams the temporal curve of the temperature and the electrical resistance of a metal oxide layer in another exemplary embodiment of the method according to the present invention.

FIG. 3 shows that resistance R is equal for two different gas mixtures G1, G2 having a different ratio of $H_2S$ and DMDS at first temperature $T_1$ and differs at second temperature $T_2$ due to a resistance profile R(G1) of first gas mixture G1 from a resistance profile R(G2) of second gas mixture G2. After temperature T has been at second temperature $T_2$ for a long time, it is increased to a third temperature $T_3$ of 325° C. After it has been at this third temperature $T_3$ for 20 seconds, it is reduced to a temperature $T_4$ of 100° C. It is apparent that the two resistance profiles R(G1), R(G2) at third temperature $T_3$ are identical to those of first temperature $T_1$ R(G1), R(G2), but differ at fourth temperature $T_4$ from those at second temperature $T_2$. In that resistance values are also measured here immediately before the reduction of third temperature $T_3$ to fourth temperature $T_4$ and also 20 seconds after the reduction of the temperature, a database is created, on the basis of which the proportion of $H_2S$ and DMDS in the gas mixture may be quantified.

Figure 4:
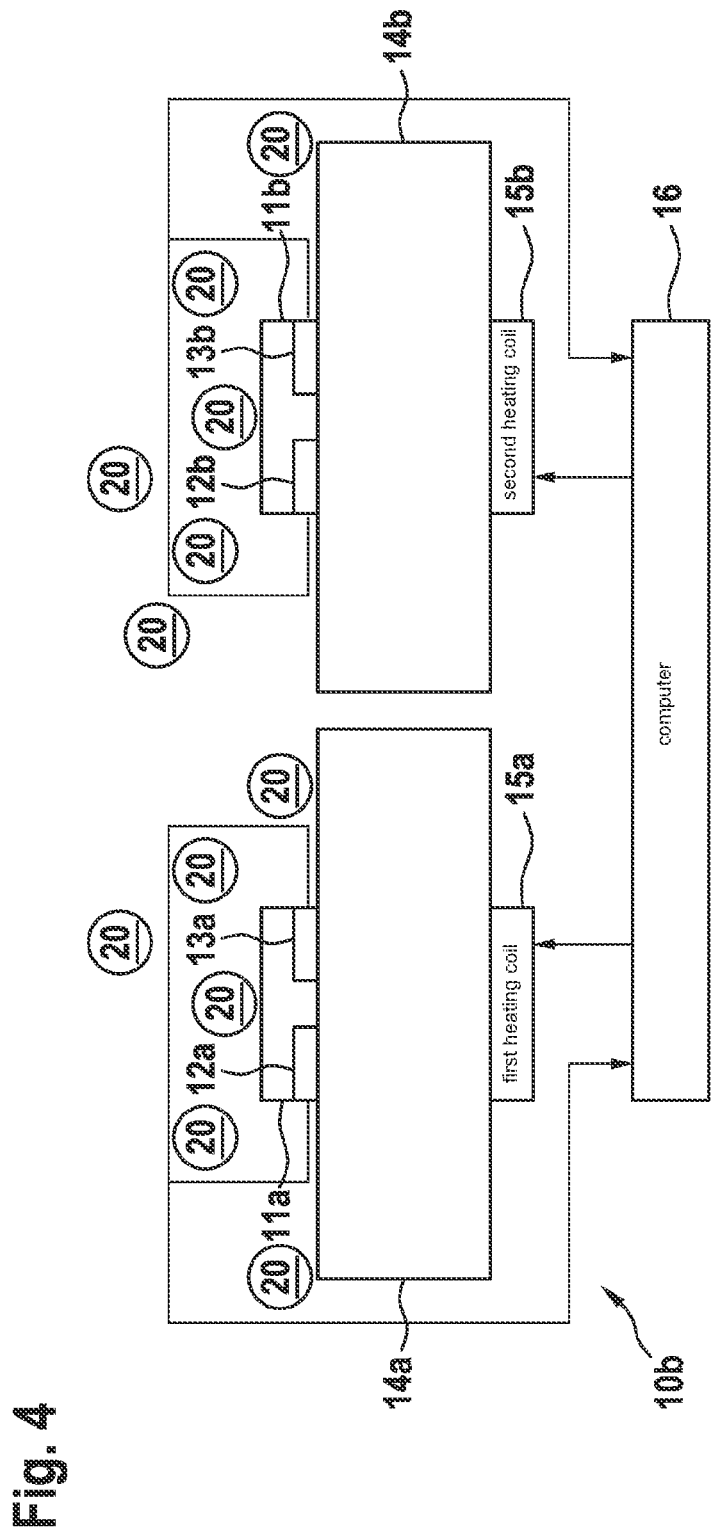
FIG. 4 schematically shows another gas sensor which may be used in an exemplary embodiment of the method according to the present invention.

FIG. 4 shows a gas sensor 10b, which may be used in a second exemplary embodiment of the method according to the present invention. It includes a first layer 11a including two electrodes 12a, 13a, a first substrate 14a, and a first heating coil 15a. Furthermore, it includes a second layer 11b including two electrodes 12b, 13b, a second substrate 14b, and a second heating coil 15b. The two substrates 14a, 14b are thermally decoupled from one another. The two heating coils 15a, 15b are activated independently of one another by a shared computer 16, which also receives the signals of all electrodes 12a, 13a, 12b, 13b. In this exemplary embodiment of the method, a single layer does not pass through the entire temperature profile according to FIG. 3. Rather, first layer 11a is only operated at first temperature $T_1$ and second temperature $T_2$ and second layer 11b is only operated at third temperature $T_3$ and at fourth temperature $T_4$. Both layers 11a, 11b are exposed to the same gas mixture. This enables a significantly faster gas analysis than with the aid of the first exemplary embodiment of the method.

Figure 5:
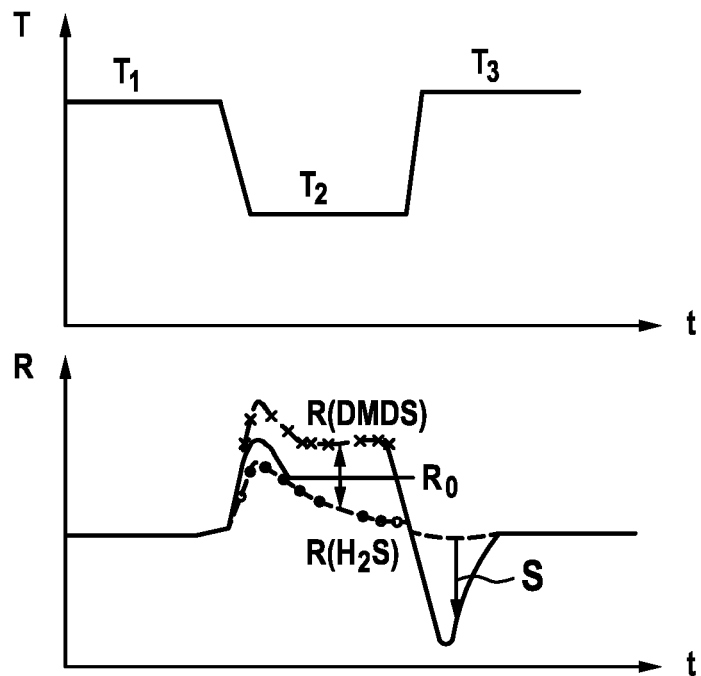
FIG. 5 shows in two diagrams the temporal curve of the temperature and the electrical resistance of a metal oxide layer in still another exemplary embodiment of the method according to the present invention.

In a third exemplary embodiment of the method, the gas sensor according to FIG. 1 is operated using the temperature profile shown in FIG. 5. Layer 11 is initially heated to a temperature $T_1$ of 300° C., then cooled to a second temperature $T_2$ of 100° C., and finally heated again to a third temperature $T_3$ of 300° C. The heating from second temperature $T_2$ to third temperature $T_3$ takes place suddenly within 100 ms. At first temperature $T_1$ and second temperature $T_2$, in this third exemplary embodiment of the method, it shows the same temperature profile for different gas mixtures as in the conventional method according to FIG. 2. $H_2S$ and DMDS would not be detectable in parallel to one another in a gas mixture under certain circumstances solely on the basis of resistance values. However, the temperature jump has the result that at a jumping point S immediately after reaching third temperature $T_3$, both $H_2S$ and DMDS have a resistance-reducing effect and thus generate a sum signal in the resistance profile. The sum signal does not have to weigh the individual signals in the ratio 1:1, but may also be a weighted sum. Even if the effects of the two sulfurous components on resistance R have eliminated one another at second temperature $T_2$, their presence may be recognized by a resistance measurement immediately after reaching third temperature $T_3$ and their portion in the gas mixture may also be quantified from the resistance value measured there together with the resistance value which was measured at second temperature $T_2$.

Figure 6:
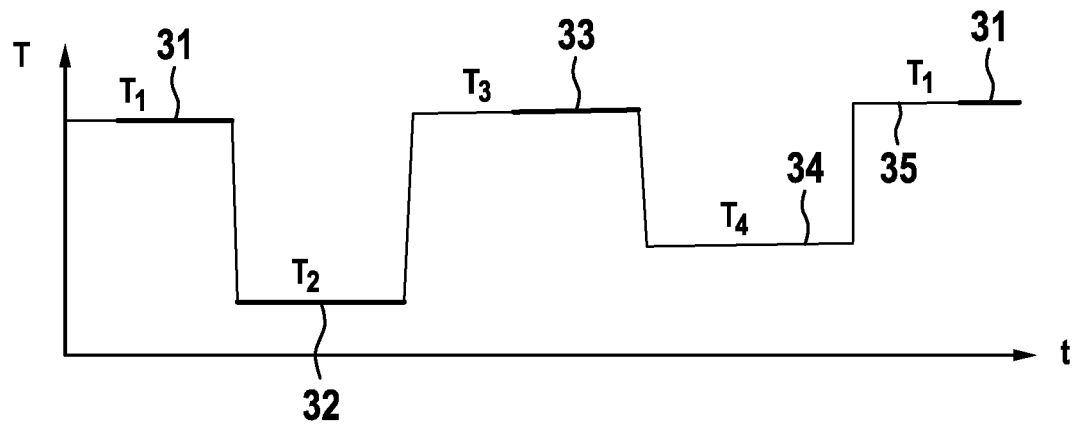
FIG. 6 shows in one diagram the temporal curve of the temperature of a metal oxide in still another exemplary embodiment of the method according to the present invention.

A fourth exemplary embodiment of the method according to the present invention follows a temperature profile which is shown in FIG. 6. Using the gas sensor according to FIG. 1, this temperature profile is periodically carried out at a period length of 80 seconds. It begins with a temperature $T_1$ of 350° C.

In a first measurement range 31, resistance values are measured, to which volatile organic components of the gas mixture, for example alcohols or ketones, provide a strong contribution. In contrast, sulfurous components only provide a small contribution. Subsequently, temperature T is reduced to a second temperature $T_2$ of 70° C. At this temperature, a second measurement range 32 is present, in which predominantly $H_2S$ provides a contribution to the measured resistance. Temperature T is subsequently increased to a third temperature $T_3$, which corresponds to first temperature $T_1$. In a third measurement range 33 at third temperature $T_3$, there is again no significant contribution of the sulfurous components of the gas mixture to the measured resistance values. Temperature T is subsequently reduced to a fourth temperature $T_4$ of 140° C. At this temperature, in a fourth measurement range 34, both $H_2S$ and DMDS contribute to the measured resistance values, the contributions of these two components having different signs. Temperature T is subsequently increased suddenly within 50 ms back to first temperature $T_1$. In a fifth measurement range 35 immediately after reaching first temperature $T_1$ again, $H_2S$ and DMDS contribute to the measured resistance values with the same sign. By periodically repeating the temperature profile according to FIG. 6, the composition of the gas mixture may be continuously monitored.

What is claimed is:

1. A method of a gas sensor for providing identifications of gases in a gas mixture, in which a layer, which is configured for the adsorption and/or absorption of components of the gas mixture, is exposed to the gas mixture, the gas sensor including a processor system that includes at least one processor, a heater, and a plurality of electrodes, the method comprising the following steps:
    in step (a), the processor system controlling the heater to set a temperature of the layer to a first temperature value;
    in step (b), measuring, by the processor system and based on electrical values of the plurality of electrodes, at least one electrical resistance value of the layer, while the temperature of the layer is at the first temperature value due to the controlling performed in step (a);
    in step (c), reducing, by the processor system, the temperature of the layer from the first temperature value due to the controlling performed in step (a) to a second temperature value;
    in step (d), measuring, by the processor system and based on the electrical values of the plurality of electrodes, at least one electrical resistance value of the layer while the layer has the second temperature due to the reducing of step (c);
    in step (e), the processor system controlling the heater to increase the temperature of the layer from the second temperature value to a third temperature value;
    in step (f), measuring, by the processor system and based on the electrical values of the plurality of electrodes, at least one electrical resistance value of the layer immediately after reaching the third temperature due to the controlling of step (e); and
    in step (g) determining and outputting an identification of a proportion of a first gas in the gas mixture based on each of the measurements of steps (b), (d), and (e) in combination and an identification of a proportion of a second gas in the gas mixture based on each of the measurements of steps (b), (d), and (e) in combination, wherein the first gas and the second gas have an opposite, and therefore a cancelling, effect on the electrical resistance in at least one temperature profile of the temperature of the layer.

2. The method as recited in claim 1, further comprising the following steps:
    in step (h), reducing the temperature of the layer from the third temperature value to a fourth temperature value; and
    in step (i), measuring at least one electrical resistance value of the layer while the layer has the fourth temperature value;
    wherein the first temperature value differs from the third temperature value and/or the second temperature value differs from the fourth temperature value.

3. The method as recited in claim 2, further comprising the following steps:
    in step (j), increasing the temperature of the layer from the fourth temperature value to the first temperature value; and
    in step (k), measuring at least one electrical resistance value of the layer while the layer has the first temperature value due to the increasing of step (i);
    wherein the determining of the identification in step (g) with respect to each of the first gas and the second gas is based additionally on the measurement of step (k).

4. The method as recited in claim 3, wherein the method is carried out periodically with a period length in a range from 20 seconds to 120 seconds.

5. The method as recited in claim 3, wherein the increase of the temperature of the layer from the second temperature value to the third temperature value in step (e) and/or the increase of the temperature of the layer from the fourth temperature value to the first temperature value in step (i) takes place within at most one second.

6. The method as recited in claim 3, wherein a gradient of the temperature increase in step (e) greater than a gradient of the temperature increase in step (j).

7. The method as recited in claim 2, wherein the measuring of each of steps (d) and (i) is performed after the layer has been held for a time period in the range of 5 seconds to 30 seconds at the respective second or fourth temperature values.

8. The method as recited in claim 2, wherein the second temperature value and the fourth temperature value are different temperature values than each other and are each in a range from 20° C. to 200° C.

9. The method as recited in claim 2, wherein the first temperature value and the third temperature value are equal to each other and are in a range from 300° C. to 400° C., the second temperature value is in a range from 30° C. to 100° C., and the fourth temperature value is in a range from 100° C. to 180° C.

10. The method as recited in claim 2, wherein:
    the determining of the identification of the first gas in the gas mixture is based on a combination of two different resistance profiles;
    the determining of the identification of the second gas in the gas mixture is based on the combination of the two different resistance profiles;
    a first of the resistance profiles is based on changes in the electrical resistance occurring by the reduction of temperature of step (c); and
    a second of the resistance profiles is based on changes in the electrical resistance occurring by the reduction of temperature of step (h).

11. The method as recited in claim 1, wherein the measuring of each of steps (b) and (f) is performed after the layer has been held for a time period of at least 100 ms at the respective first temperature or third temperature values.

12. The method as recited in claim 1, wherein the first temperature value and the third temperature value are different temperature values than each other and are each in a range from 250° C. to 400° C.

13. The method as recited in claim 1, wherein each of the first gas and the second gas contains a sulfurous component.

14. The method as recited in claim 1, wherein the first gas is hydrogen sulfide and the second gas is dimethyl disulfide.

15. The method as recited in claim 1, wherein a gradient of the temperature change of step (e) is greater than a gradient of the temperature change of step (c).

16. A gas sensor, which is configured to provide identifications of gases in a gas mixture, the gas sensor comprising:
    a processor system that includes at least one processor, a heater, and a plurality of electrodes; and
    a layer configured for adsorption and/or absorption of components of the gas mixture; and
    wherein:
        the at least one processor is configured to:

in step (a), control the heater to set a temperature of the layer to a first temperature value;

in step (b), measure, based on electrical values of the plurality of electrodes, at least one electrical resistance value of the layer, while the temperature of the layer is at the first temperature value due to the controlling performed in step (a);

in step (c), reduce the temperature of the layer from the first temperature value due to the control performed in step (a) to a second temperature value;

in step (d), measure, based on the electrical values of the plurality of electrodes, at least one electrical resistance value of the layer while the layer has the second temperature due to the reducing of step (c);

in step (e), control the heater to increase the temperature of the layer from the second temperature value to a third temperature value;

in step (f), measure, based on the electrical values of the plurality of electrodes, at least one electrical resistance value of the layer immediately after reaching the third temperature due to the controlling of step (e); and in step (g) determine and output an identification of a proportion of a first gas in the gas mixture based on each of the measurements of steps (b), (d), and (e) in combination and an identification of a proportion of a second gas in the gas mixture based on each of the measurements of steps (b), (d), and (e) in combination; and the first gas and the second gas have an opposite, and therefore a cancelling, effect on the electrical resistance in at least one temperature profile of the temperature of the layer.

* * * * *